_United States Patent_ [19]

Karpiel

[11] Patent Number: 5,024,617
[45] Date of Patent: Jun. 18, 1991

[54] SPHINCTEROTOMY METHOD AND DEVICE HAVING CONTROLLED BENDING AND ORIENTATION

[75] Inventor: John Karpiel, Winston-Salem, N.C.

[73] Assignee: Wilson-Cook Medical, Inc., Winston-Salem, N.C.

[21] Appl. No.: 318,724

[22] Filed: Mar. 3, 1989

[51] Int. Cl.$^5$ ............................................. A61B 17/36
[52] U.S. Cl. ....................................................... 606/47
[58] Field of Search ................... 128/772; 604/95, 280, 604/282; 606/39, 45, 46, 47, 113, 129, 170

[56] References Cited

U.S. PATENT DOCUMENTS

| | | | |
|---|---|---|---|
| 3,552,384 | 1/1971 | Pierie | 604/95 |
| 4,325,374 | 4/1982 | Komiya | 128/303.15 |
| 4,474,174 | 10/1984 | Petruzzi | 128/4 |
| 4,485,812 | 12/1984 | Harada et al. | 128/303.15 |
| 4,545,390 | 10/1985 | Leary | 128/772 |
| 4,724,836 | 2/1988 | Okada | 128/303.15 |
| 4,807,626 | 2/1989 | McGirr | 128/772 |

OTHER PUBLICATIONS

Wilson-Cook Medical Inc. product information brochure, 1988.
Waye, J., Geenen, J., Fleischer, D., and Venu, R., "Techniques in Therapeutic Endoscopy", _Endoscopic Sphincterotomy,_ Wilson-Cook Medical Inc., 1987.

_Primary Examiner_—Max Hindenburg
_Attorney, Agent, or Firm_—Woodard, Emhardt, Naughton Moriarty & McNett

[57] ABSTRACT

A sphincterotome, such as a papillotome, is disclosed for surgical cutting using an electrically conductive cutter wire. The sphincterotome includes a multi-lumen tubular member, with one lumen having an electrical conductor disposed therein, and the other lumen having a reinforcing wire disposed therein. The reinforcing wire is preferably rectangular in cross-section, providing a greater moment of inertia in a resisting axis than in a bending axis. Accordingly, the cutting edge of the cutting wire may be oriented to the 12 o'clock position of the papillary orifice to avoid injury to the duodenal wall or pancreatic duct in the patient, and to maintain the cutting edge in a predetermined cutting plane. Fluoroscopic indicating stripes may be provided at the distal end of the sphincterotome. A method of use and method of fabrication of the present invention is also disclosed.

13 Claims, 5 Drawing Sheets

SPHINCTEROTOMY METHOD AND DEVICE HAVING CONTROLLED BENDING AND ORIENTATION

BACKGROUND OF THE INVENTION

The present invention relates generally to sphincterotomy, and more specifically to devices such as papillotomes and their method of use and fabrication to provide controlled bending during cutting to provide controlled cutting of the patient's sphincter.

In endoscopic sphincterotomy, sphincterotomes, and more specifically papillotomes, are used in conjunction with an endoscope to provide surgical cutting inside of a patient. For example, the Sphincter of Oddi opens into the duodenum at the Papilla of Vater, with the common bile duct and the pancreatic duct merging into a common channel, the Ampulla of Vater. A papillotome may be used to partially cut open the Papilla of Vater for treatment such as removal of common bile duct stones forming an obstruction.

Unfortunately, complications can arise from endoscopic sphincterotomy. For example, a survey was conducted by the American Society for Gastrointestinal Endoscopy in which endoscopic sphincterotomy was attempted in 5,790 patients. Of these, 393 patients had complications, and 22 patients died. This mortality rate of about 0.04 percent is serious. Major complications from endoscopic sphincterotomy include bleeding, pancreatitis, perforation, and cholangitis, with bleeding being the most common complication. The vast majority of such bleeding typically results when the retroduodenal artery is cut. The present invention enhances the control which a physician has in performing a sphincterotomy, and provides a reduced risk of inadvertent or uncontrolled cuts which may injure the patient.

Earlier papillotomes, such as disclosed in U.S. Pat. No. 4,485,812 to Harada et al. disclose a papillotome of the general type having an electrically conductive wire exposed outside of a tube to act as a cutter. A variety of such sphincterotomes with the wire formed in a bow outside the tube are known as soma or push-type sphincterotomes, as well as traction-type sphincterotomes. These devices generally are well known, but may contribute to the problem previously described. Shortcomings of this type of papillotome are discussed in U.S. Pat. No. 4,474,174 to Petruzzi, rejecting these more conventional papillotome knives as lacking precise control and providing poor control with danger to adjacent structures during cutting. Instead, the Petruzzi patent suggests an alternative approach in which, rather than having a bowed cutting wire, a pre-bent wire knife having a distal tip is advanced inside a single lumen catheter until it projects from a channel cut through the catheter wall at an angle. The wire knife is connected to a control wire which is manipulated to extend and retract the wire knife to engagement with the tissue. The control wire is fabricated from a helically twisted ribbon-shaped wire. The helically twist provides both a passage way through the lumen for the supply of contrast media, and prevents radial collapse of the catheter walls to maintain the lumen open.

Several other cutting devices have been proposed with a variety of twisted reinforcing wires or other reinforcing wires in the catheter lumen to reinforce against radial collapse to maintain the lumen open to allow fluids, such as contrast media, to be supplied to the surgical area. Such devices are illustrated in U.S. Pat. No. 4,325,374 to Komiya, in which a coiled spring is utilized to prevent lumen collapse; and U.S. Pat. No. 4,724,836 to Okada in which a reinforcing wire is disposed in a fluid lumen to prevent collapse of the lumen when the distal tip is bent. Although these various reinforcing wires may be advantageous for preventing collapse of the lumen, they are not directed to solving the problem set forth above regarding uncontrolled cutting.

One approach to this problem was conceived by Dr. Frimberger in Munich, Germany, to wedge a ribbon of spring steel into the distal 15 to 20 centimeters of the lumen of the papillotome. Unfortunately, such device presented manufacturing problems and was problematic in that the papillotome would exit the endoscope in the proper orientation only about 70 or 80 percent of the time.

The present invention overcomes the limitations of other devices and provides for a controlled, safer cutting. Furthermore, the device of the present invention exits the endoscope in the correct orientation virtually all of the time. Accordingly, the risk of complications, and the associated mortality, may be reduced. The present invention provides a specially oriented reinforcing member disposed in a second lumen in the sphincterotome. Preferably, this reinforcing member has a rectangular cross-section and runs the entire length of the lumen. Due to the rectangular cross-sectional shape, there is a greater cross-sectional moment of inertia along a bending axis than along a perpendicular axis. This provides controlled rigidity in one dimension, allowing the cutting edge of the cutter wire to be moved in a predetermined cutting plane. This cutting plane may be properly oriented with respect to the sphincter to be cut due to this controlled rigidity. Accordingly, the physician maintains a greater control during endoscopic sphincterotomy, and reduces the risk of improper cuts and the associated complications. Furthermore, the present invention is well suited for quality control manufacturing to ensure cutting in the proper plane when the device is used. Accordingly, the present invention provides a significant advance in the art.

SUMMARY OF THE INVENTION

The present invention provides a medical sphincterotome, comprising an elongated multi-lumen tubular member having a proximal end and a distal end and being sized to be received in an endoscopic lumen; a cutter having a cutting edge located along the distal end of the tubular member and oriented generally longitudinally with respect to the tubular member, wherein the cutting edge is movable in a cutting plane to cut a patient's sphincter, the cutter being connected to a conductor disposed in a first longitudinal lumen in the tubular member; a second longitudinal lumen along the length of the tubular member for receiving reinforcing means; and reinforcing means disposed in the second longitudinal lumen for resisting movement of the cutting edge out of the cutting plane, the reinforcing means having a first cross-sectional moment of inertia with respect to a bending axis normal to the cutting plane, the reinforcing means further having a second cross-sectional moment of inertia with respect to a resisting axis lying along the cutting plane and generally perpendicular to the tubular member, wherein the second moment of inertia is greater than the first moment of inertia along the distal end to resist bending out of the cutting plane to provided controlled cutting of the patient's sphincter along the cutting plane.

The present invention further provides a method of surgically cutting a patient's sphincter, comprising the steps of positioning an endoscope near the sphincter to allow viewing of the sphincter; extending a sphincterotome out of an opening in the endoscope and into engagement with the sphincter, the sphincterotome comprising an elongated multi-lumen tubular member having a proximal end and a distal end and being sized to be received in an endoscopic lumen; a cutter having a cutting edge located along the distal end of the tubular member and oriented generally longitudinally with respect to the tubular member, wherein the cutting edge is movable in a cutting plane to cut the patient's sphincter, the cutter being connected to a conductor disposed in a first longitudinal lumen in the tubular member; a second longitudinal lumen along the length of the tubular member for receiving reinforcing means; and reinforcing means disposed in the second longitudinal lumen for resisting movement of the cutting edge out of the cutting plane, the reinforcing means having a first cross-sectional moment of inertia with respect to a bending axis normal to the cutting plane, the reinforcing means further having a second cross-sectional moment of inertia with respect to a resisting axis lying along the cutting plane and generally perpendicular to the tubular member, wherein the second moment of inertia is greater than the first moment of inertia along the distal end to resist bending out of the cutting plane; orienting the cutting edge and the reinforcing means so that the cutting plane is oriented radially with respect to a center of the sphincter; and energizing the cutter with the cutting edge in the cutting plane to cut the sphincter radially outward of the center of the sphincter while the reinforcing means resists movement of the cutting edge out of the cutting plane.

The present invention further provides a method of fabricating a medical sphincterotome, comprising the steps of extruding an elongated multi-lumen tubular member having a first longitudinal lumen and a second longitudinal lumen, the tubular member having a small outer cross-sectional dimension receivable in an endoscopic lumen, the second lumen in the tubular member being cross-sectionally rectangular with a height and a width greater than the height; locating a reinforcing wire having a rectangular cross-section in and corresponding to the second longitudinal lumen substantially along the entire length of the lumen; locating a cutter having a conductor through the first longitudinal lumen and forming a cutter bow with the cutter at a distal end of the tubular member between first and second locations outside of the first lumen; and affixing means for manipulating the cutter to a proximal end of the tubular member.

One object of the present invention is to provide an improved sphincterotomy method and device having controlled bending.

Another object of the present invention is to provide a method of fabricating a sphincterotome having the benefits described herein.

Another object of the present invention is to reduce complications associated with endoscopic sphincterotomy.

Another object of the present invention is to reduce undesirable bleeding during papillotomy.

Another object of the present invention is to provide a sphincterotome having a cutter consistently oriented to the 12 o'clock position of the papillary orifice to avoid injury to the duodenal wall or pancreatic duct.

These and other objects and benefits of the present invention will be apparent from the following specification and drawings.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated method and device, and such further applications of the principles of the invention as illustrated therein being contemplated as would normally occur to one skilled in the art to which the invention relates.

Figure 1:
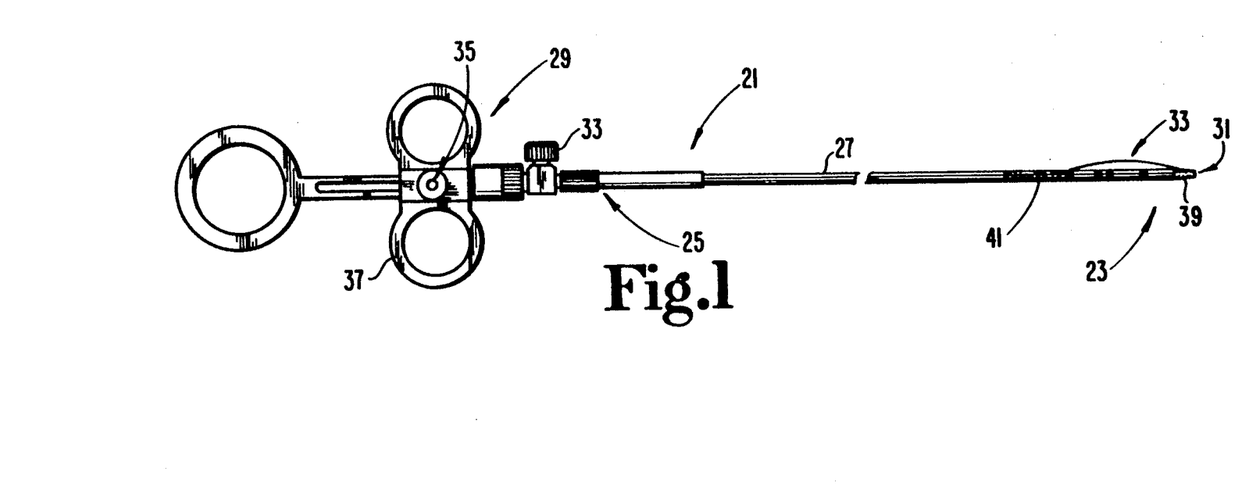
FIG. 1 is a side view of a sphincterotome according to the present invention.

Referring now to FIGS. 1-8, like reference characters correspond to like elements. Sphincterotome 21 is illustrated having distal end 23 and proximal end 25. Referring to FIG. 1, sphincterotome 21 includes a tubular member 27 and a manipulator control handle 29 connected to the proximal end of tubular member 27 by adhesive or other such means. Tubular member 27 preferably is a multi-lumen five French catheter extruded from tetrafluoroethelene (Teflon). Preferably there are two lumens as discussed further below. One lumen may have an opening 31 at the distal end of the tubular member, with the lumen at its proximal end being coupled to fitting 33. Fitting 33 may be coupled to a supply of fluid, such as fluoroscopic contrast media, to supply the contrast media out through opening 31 and into the patient. Furthermore, this lumen may have a wire disposed through it making up an electrically conductive cutter 33 at the distal end of tubular member 27. Cutter 33 is preferably wire running through the lumen as electrical conductor 43 which is connected at its proximal end to connection 35 to provide a high frequency electrical current to cutter 33 as is well known. Manipulator control handle 29 may include handle 37 which may be drawn proximally to exert traction on the conductor wire to cause cutter 33 to pull tight as is known. Note that in FIG. 1, tubular member 27 is shown broken for drawing clarity, but in at least one embodiment it is about 200 centimeters long.

Optionally, distal end 23 of the sphincterotome includes fluoroscopic indicating stripes, such as indicating stripe 39 and indicating stripe 41. Three narrower bands of indicator stripes are illustrated as well.

Figure 2:
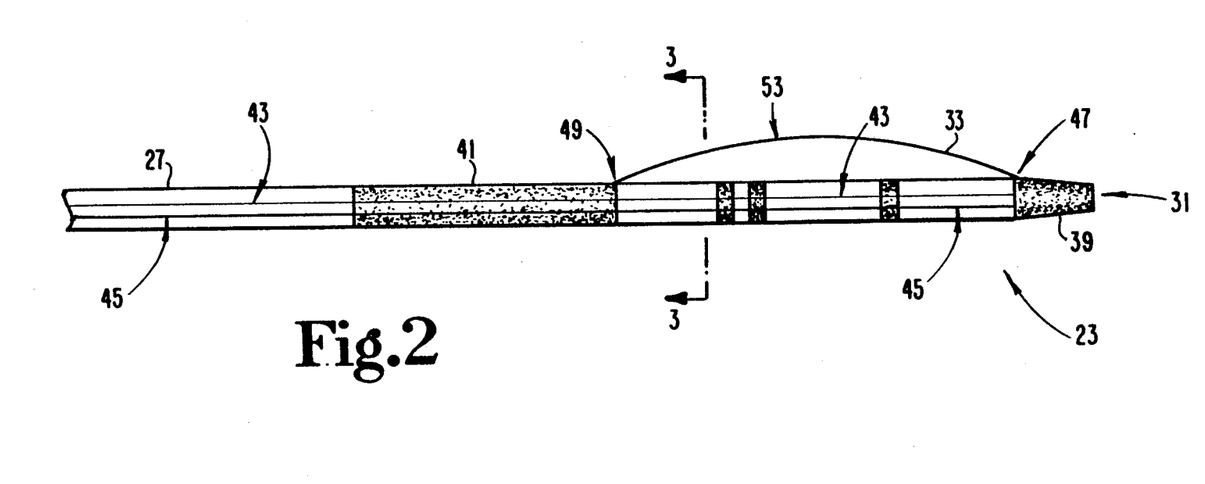
FIG. 2 is an enlarged detailed view of a distal end of the device of FIG. 1.

Referring to FIG. 2, distal end 23 of sphincterotome 21 is illustrated. Tubular member 27 may be made of a transparent or at least translucent material. Accordingly, electrical conductor 43 and reinforcing wire 45 may be seen through tubular member 27. Preferably, electrical conductor 43 and cutter 33 are all formed from a single strand of small braided wire. Conductor 43 is disposed in a first lumen in tubular member 27 running from the proximal end to the distal end and protrudes outward of the wall of tubular member 27 through an opening 51 (see FIG. 4) to become cutter 33. Cutter 33 is bowed between a first location 47 and a second location 49 on the outside of the lumen in tubular member 27. Cutter 33 re-enters the wall of tubular member 27 and doubles back in a distal direction through the first lumen for several centimeters to its free end (not shown). Cutter 33 has cutting edge 53 which is located along the distal end of tubular member 27 between first location 47 and second location 49. Cutting edge 53 is shown oriented generally longitudinal with respect to tubular member 27 and is oriented radially outwardly to engage the tissue to be cut in the patient.

Figure 3:
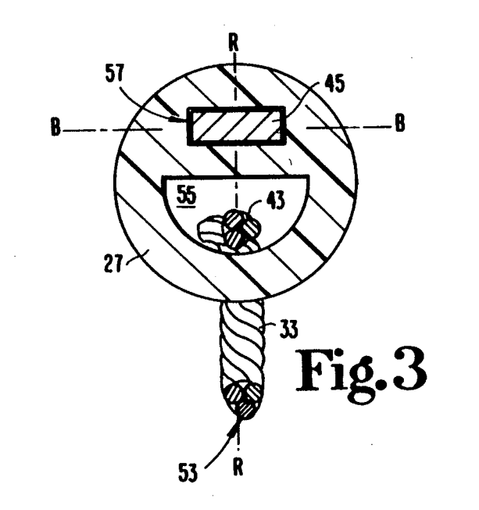
FIG. 3 is a cross-sectional view (inverted) taken along line 3—3 in FIG. 2.
Figure 4:
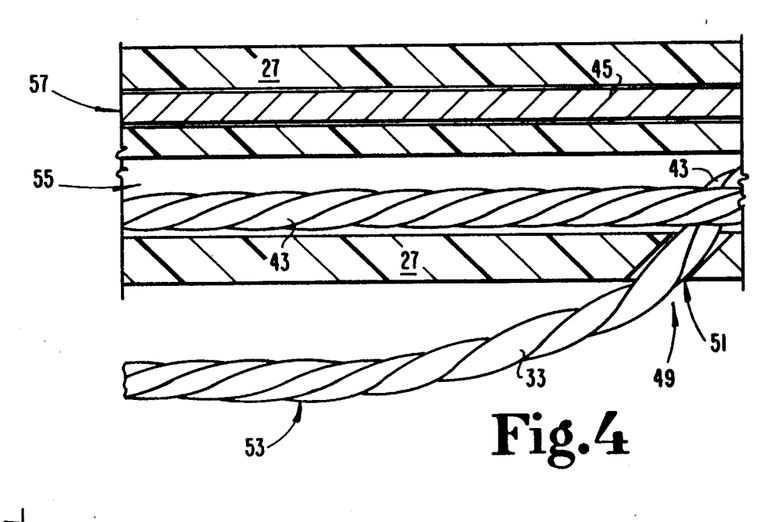
FIG. 4 is a partial side sectional view of the device of the present invention.
Figure 5:
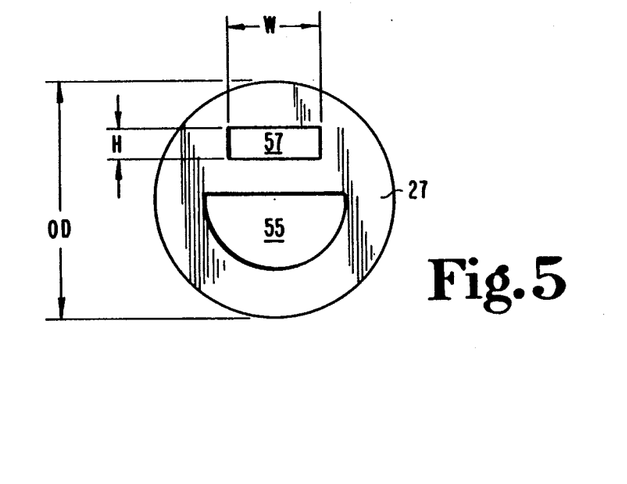
FIG. 5 is a typical cross-sectional view of a tubular member fabricated and utilized in the present invention.

Referring to FIGS. 3, 4 and 5, a more detailed illustration of the construction of the present invention is shown. Electrical conductor wire 43 is shown disposed in a first longitudinal lumen 55. Lumen 55 is shown with a half-circle cross-sectional shape, or may be round or otherwise, and is preferably significantly larger than conductor wire 43 to allow wire 43 to move in the lumen and to allow passage of fluid, such as contrast media.

Reinforcing wire 45 is preferably made of spring steel and is disposed in a second longitudinal lumen 57, preferably along the entire length of lumen 57. As illustrated, lumen 57 and reinforcement wire preferably are rectangular in shape, both having a width W and a height H (see FIG. 5), with width W being greater than height H.

Figure 6:
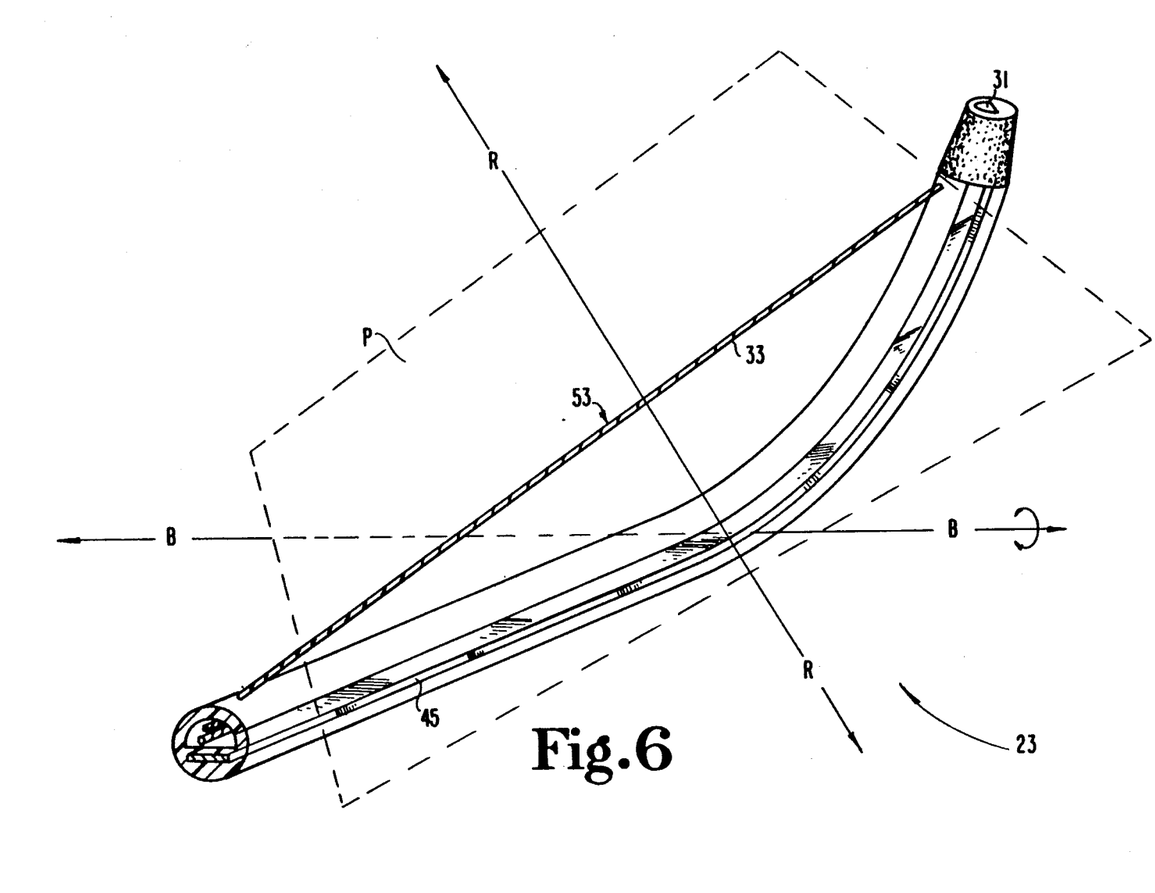
FIG. 6 is a perspective partial view of the distal end of the device of the present invention showing a cutting plane, a bending axis, and a resisting axis superimposed thereon.
Figure 7:
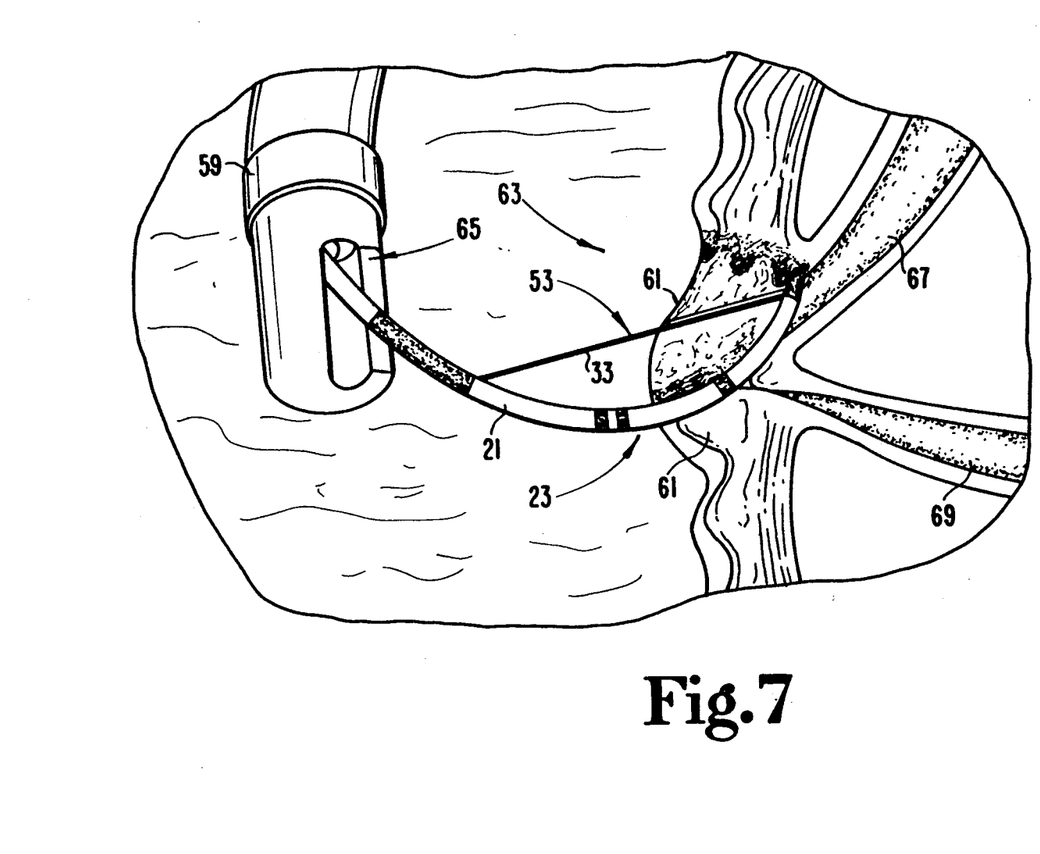
FIG. 7 is a partial view of the present invention being utilized to perform endoscopic sphincterotomy on the Sphincter of Oddi in the Papillia of Vater.

Referring to FIGS. 3 and 6, bending axis B and resisting axis R are shown. Resisting axis R is shown lying in cutting plane P, whereas bending axis B is shown perpendicular to axis R and normal to cutting plane P (see FIG. 6). Cutter 33's cutting edge 53 also lies in cutting plane P. Upon manipulation of control handle 29, cutting edge 53 is movable in cutting plane P to cut a patient's sphincter. Such movement is caused in the present embodiment by tensioning of conductor wire 43 which pulls on cutter 33 through opening 51, causing distal location 47 to be drawn proximally and causing cutting edge 53 to sweep through cutting plane P. Although bending occurs about bending axis B, conversely, bending is resisted about resisting axis R. This is due to the cross-sectional shape of reinforcing wire 45, and more specifically to the cross-sectional moment of inertias of reinforcing wire 45 about axis B and about axis R. The cross-sectional moment of inertia about axis B, $I_B$, and the cross-sectional moment of inertia about axis R, $I_R$, are determined for a rectangular shape by the following equations:

$$I_B(\text{in.}^4) = \frac{WH^3}{12}$$

$$I_R(\text{in.}^4) = \frac{HW^3}{12}$$

As can be seen from the foregoing equations, since width W is greater than height H, $I_R$ is greater than $I_B$. Accordingly, there is greater resistance to bending about axis R than there is about axis B. Although the preferred embodiment utilizes rectangular wires as illustrated, other reinforcing members may be utilized with different geometries so long as $I_R$ is greater than $I_B$. Note further that bending axis B is determined with respect to reinforcing wire 45 in the illustrations, rather than with respect to the entire sphincterotome 21 including tubular member 27. In the preferred embodiment, width W is about 0.026 inches, and height H is about 0.009 inches. Furthermore, reinforcing wire 45 provides greater torsional rigidity thereby helping to ensure that the sphincterotome exits the endoscope in the proper 12 o'clock orientation (see FIG. 8). The outer dimension OD of tubular member 27 is relatively small and suitably sized to fit in an endoscopic lumen. In the preferred embodiment, outside dimension OD is about 0.066 inches. Furthermore, in the preferred embodiment, tubular member 27, lumen 55, lumen 57, reinforcing wire 45, and cutting edge 53 are all symetrically disposed along cutting plane P.

Figure 8:
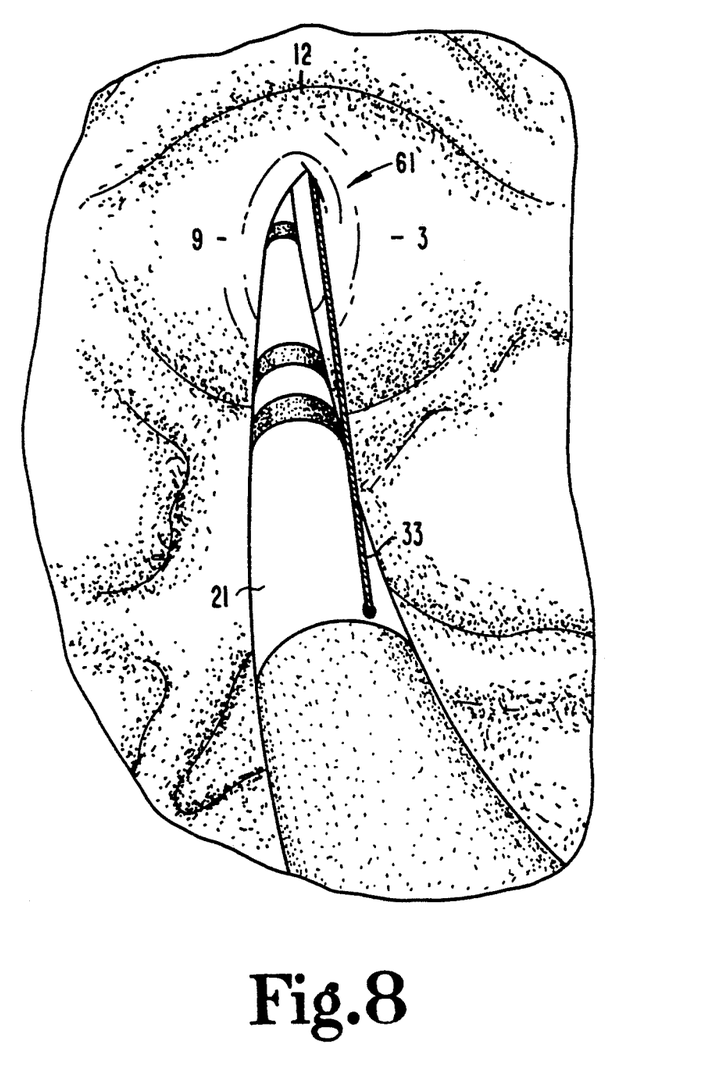
FIG. 8 is a view from an endoscope of the present invention being utilized to perform endoscopic sphincterotomy on the Sphincter of Oddi in the Papillia of Vater with the cutter in the 12 o'clock position.

Referring again to FIGS. 1-8, and particularly FIGS. 7 and 8, the method of use of the present invention is as follows. An endoscope 59 is advanced into the patient and positioned near the Sphincter of Oddi 61 in the Papilla of Vater 63. Endoscope 59 is positioned to allow viewing of sphincter 61 as is known. Next, sphincterotome 21 is extended out of opening 65 in endoscope 59. Sphincterotome 21 is extended into engagement with sphincter 61 by inserting the distal end 23 into the Ampulla of Vater which communicates with the common bile duct 67 and the pancreatic duct 69. Cutting edge 53 and the reinforcement wire 45 are oriented in the center of sphincter 61 so that the cutting plane is oriented radially with respect to the central Ampulla of Vater. More specifically, this orientation is such that cutter wire 33 is oriented to the 12 o'clock position of the papillary orifice to avoid injury to the duodenal wall or pancreatic duct. The 12 o'clock position is illustrated in FIG. 8, showing encircled 12, 3, and 9 corresponding to the positions of twelve o'clock, three o'clock, and nine o'clock respectively on a clock face and around sphincter 61. When sphincterotome 21 is viewed from the endoscope, as shown in FIG. 8, the cutter 33 is positioned in the 12 o'clock position to avoid injury with the rigidity provided by reinforcing wire 45 aiding the proper positioning. Note that in the illustrated endoscope, the viewing occurs along side of the sphinterotome, and accordingly in FIG. 8 sphincterotome 21 is shown somewhat to the right of the viewer's perspective and sphincter 61 is viewed somewhat off center.

Manipulator handle 29 is utilized to gradually tighten cutter 33 to a partially flexed position so approximately half of cutter 33 is visible outside the papillary orifice. Cutter 33 is electrically energized as is known to cut sphincter 61 radially outward of the center of the sphincter while reinforcing wire 45 resists movement of cutting edge 53 out of the cutting plane P.

Reinforcing wire 45, and its rigidity against bending out of cutting plane P provides significant improvement in the orientation of cutting edge 53 in the 12 o'clock position as distal end 23 of the sphincterotome is advanced out of opening 65 of endoscope 59.

The method of fabrication of the present invention is largely apparent from the foregoing description and drawings. Referring to FIG. 5, tubular member 27 is extruded from Teflon, such as by conventional extruding techniques used in the catheter industry. Specifically, tubular member 27 is preferably formed with two lumens, although conceivably more lumens may be utilized. Lumen 57 as illustrated is in rectangular shape to snugly receive reinforcing wire 45. Lumen 55 has a half-circle cross-sectional shape. In one version, tubular member 27 is fabricated 210 centimeters long. Thereafter, reinforcing wire 45 is located in lumen 57 by inserting it therethrough from one end, and is preferably located substantially along the entire length of lumen 57. Alternatively, it is possible to extrude tubular member 27 simultaneously with reinforcing wire 45 imbedded therein, particularly with lumen 55 being round.

Conductor 34 is threaded through lumen 55 from one end of the tubular member to another. Cutter 33 is formed under a cutter bow as illustrated by passing one free end of conductor 34 is threaded through opening 51 (see FIG. 4) in the wall of lumen 55 outward of such lumen. A conventional cutter bow is formed between location 49 and location 47 where the wire is reinserted, such as through an opening in the catheter wall, into lumen 55 and secured thereto. For example, the free end of the wire may be threaded proximally back through lumen 55. Accordingly, cutter 33 is formed as a cutter bow. The proximal end of conductor 34 is attached to electrical connection 35 and handle 37 as is known in the proximal end 25 of tubular member 27 is affixed to manipulator control handle 29 using adhesive or other such means. Alternatively, the device and method of the present invention may use a bow configuration of the push-type or hump bow style cutters. Accordingly, the present invention may be conveniently made.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical sphincterotome, comprising:
   an elongated multi-lumen tubular member having a proximal end and a distal end and being sized to be received in an endoscopic lumen;
   a cutter having a cutting edge located along said distal end of said tubular member and oriented generally longitudinally with respect to said tubular member, wherein said cutting edge is movable in a cutting plane to cut a patient's sphincter, said cutter being connected to a conductor disposed in a first longitudinal lumen in said tubular member;
   a second longitudinal lumen along the length of said tubular member for receiving reinforcing means; and
   reinforcing means disposed in said second longitudinal lumen for resisting movement of said cutting edge out of said cutting plane, said reinforcing means having a first cross-sectional moment of inertia with respect to a bending axis normal to said cutting plane, said reinforcing means further having a second cross-sectional moment of inertia with respect to a resisting axis lying along said cutting plane and generally perpendicular to said tubular member, wherein said second moment of inertia is greater than said first moment of inertia along said distal end to resist bending out of said cutting plane to provided controlled cutting of the patient's sphincter along said cutting plane.

2. The sphincterotome of claim 1 wherein said reinforcing means comprises a cross-sectionally rectangular wire.

3. The sphincterotome of claim 2 wherein said second longitudinal lumen has a rectangular cross-section corresponding to the cross-section of said reinforcing means.

4. The sphincterotome of claim 3 wherein said first longitudinal lumen has an opening at said distal end of said tubular member.

5. The sphincterotome of claim 4 and further comprising indicating means at said distal end of said tubular member for providing visual indication of the position of said distal end in the patient.

6. The sphincterotome of claim 5 wherein said cutter comprises a wire bowed between first and second locations at said distal end outside of said first longitudinal lumen.

7. The sphincterotome of claim 1 wherein said second longitudinal lumen has a rectangular cross-section.

8. The sphincterotome of claim 1 wherein said first longitudinal lumen has an opening at said distal end of said tubular member.

9. The sphincterotome of claim 1 and further comprising indicating means at said distal end of said tubular member for providing visual indication of the position of said distal end in the patient.

10. The sphincterotome of claim 1 wherein said cutter comprises a wire bowed between first and second locations at said distal end outside of said first longitudinal lumen.

11. A method of surgically cutting a patient's sphincter, comprising the steps of:
    positioning an endoscope near the sphincter to allow viewing of the sphincter;
    extending a sphincterotome out of an opening in said endoscope and into engagement with the sphincter, said sphincterotome comprising:
    an elongated multi-lumen tubular member having a proximal end and a distal end and being sized to be received in an endoscopic lumen; a cutter having a cutting edge located along said distal end of said tubular member and oriented generally longitudinally with respect to said tubular member, wherein said cutting edge is movable in a cutting plane to cut the patient's sphincter, said cutter being connected to a conductor disposed in a first longitudinal lumen in said tubular member; a second longitudinal lumen along the length of said tubular member for receiving reinforcing means; and reinforcing means disposed in said second longitudinal lumen for resisting movement of said cutting edge out of said cutting plane, said reinforcing means having a first cross-sectional moment of inertia with respect to a bending axis normal to said cutting plane, said reinforcing means further having a second cross-sectional moment of inertia with respect to a resisting axis lying along said cutting plane and generally perpendicular to said tubular member, wherein said second moment of inertia is greater than said first moment of inertia along said distal end to resist bending out of said cutting plane;

orienting said cutting edge and said reinforcing means so that said cutting plane is oriented radially with respect to a center of the sphincter; and energizing said cutter with said cutting edge in said cutting plane to cut the sphincter radially outward of said center of the sphincter while said reinforcing means resists movement of said cutting edge out of said cutting plane.

12. The method of claim 11 wherein said reinforcing means comprises a cross-sectionally rectangular wire.

13. The method of claim 11 wherein said sphincter is the Sphincter of Oddi in the Papilla of Vater.

* * * * *